United States Patent
Zhao et al.

(10) Patent No.: US 9,632,086 B2
(45) Date of Patent: Apr. 25, 2017

(54) METHOD AND KIT FOR DETERMINING-ANTIBODY SENSITIVITY AND CLONE CELL STRAIN

(71) Applicant: Shenzhen Mindray Bio-Medical Electronics Co., Ltd., Shenzhen (CN)

(72) Inventors: Yumei Zhao, Shenzhen (CN); Lifang Dong, Shenzhen (CN); Ting Lei, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 191 days.

(21) Appl. No.: 14/319,056

(22) Filed: Jun. 30, 2014

(65) Prior Publication Data

US 2014/0371090 A1 Dec. 18, 2014

Related U.S. Application Data (63) Continuation of application No. PCT/CN2012/086596, filed on Dec. 13, 2012.

(30) Foreign Application Priority Data

Dec. 31, 2011 (CN) .......................... 2011 1 0459537

(51) Int. Cl.
| | | |
|---|---|---|
| *G01N 33/554* | (2006.01) | |
| *C07K 16/00* | (2006.01) | |
| *G01N 33/569* | (2006.01) | |
| *G01N 33/68* | (2006.01) | |
| *C07K 16/28* | (2006.01) | |

(52) U.S. Cl.
CPC ....... *G01N 33/56972* (2013.01); *C07K 16/00* (2013.01); *C07K 16/2803* (2013.01); *C07K 16/2809* (2013.01); *C07K 16/289* (2013.01); *C07K 16/2812* (2013.01); *G01N 33/554* (2013.01); *G01N 33/6854* (2013.01); *G01N 2333/7051* (2013.01); *G01N 2333/70514* (2013.01); *G01N 2333/70589* (2013.01); *G01N 2333/70596* (2013.01)

(58) Field of Classification Search
CPC ........... G01N 33/56972; G01N 33/554; G01N 33/6854; G01N 2333/7051; G01N 2333/70514; G01N 2333/70589; G01N 2333/70596; C07K 16/00; C07K 16/2803; C07K 16/2809; C07K 16/2812; C07K 16/289

See application file for complete search history.

(56) References Cited

U.S. PATENT DOCUMENTS

| | | | |
|---|---|---|---|
| 4,275,053 A | | 6/1981 | Rosenfield et al. |
| 4,608,246 A | * | 8/1986 | Bayer .................... G01N 33/53 435/23 |
| 4,816,413 A | | 3/1989 | Sinor et al. |
| 6,461,825 B1 | * | 10/2002 | Carriere ............... G01N 33/545 435/7.24 |
| 9,133,506 B2 | * | 9/2015 | Katzir .................. C12Q 1/6841 |
| 9,291,628 B2 | * | 3/2016 | Leonard .............. B01L 3/50857 |

FOREIGN PATENT DOCUMENTS

| | | |
|---|---|---|
| CN | 1188115 A | 7/1998 |
| CN | 1545621 A | 11/2004 |
| CN | 1660907 A | 8/2005 |
| CN | 1693461 A | 11/2005 |
| CN | 1718588 A | 1/2006 |
| CN | 101044404 A | 9/2007 |
| CN | 101246173 A | 8/2008 |
| CN | 101665781 A | 3/2010 |
| CN | 101793897 A | 8/2010 |
| CN | 101891806 A | 11/2010 |
| WO | WO85/01354 A1 | 3/1985 |

* cited by examiner

*Primary Examiner* — Gail R Gabel
(74) *Attorney, Agent, or Firm* — Kory D. Christensen; Stoel Rives LLP (57) ABSTRACT

A method and kit for determining antibody sensitivity and quality of a clone cell stain. The method comprises: obtaining a solid-phase carrier, cells and an antibody; adsorbing the antibody on the solid-phase carrier; incubating the cells and the antibody; preserving cells bound with the antibody; and dyeing and counting the cells bound with the antibody, so as to determine the antibody sensitivity or the quality of the clone cell stain based on the cell count. The kit comprises components used in the method.

17 Claims, 9 Drawing Sheets

МЕТHOD AND KIT FOR
DETERMINING-ANTIBODY SENSITIVITY
AND CLONE CELL STRAIN

RELATED APPLICATION

This application claims priority to Chinese Patent Application No. 201110459537.0, filed on Dec. 31, 2011, the disclosure of which is fully incorporated herein by reference.

TECHNICAL FIELD

The present disclosure relates to the field of antibody technology, more particularly to techniques for determining antibody sensitivity, and methods for determining positive cloned cell strains which secretes object antibodies in an antibody preparing process.

BRIEF SUMMARY

The present disclosure relates to a method and kit for determining antibody sensitivity or positive cloned cell strain using cells, particularly using proteins having natural conformation on the surface of cells.

In one aspect of the present disclosure, a method for determining antibody sensitivity is provided that can include:
  obtaining a solid-phase carrier, cells and an antibody;
  adsorbing the antibody on the solid-phase carrier;
  incubating the cells and the antibody;
  preserving cells bound with the antibody;
  dyeing and counting the cells bound with the antibody; and
  determining the antibody sensitivity based on the cell count.

In another aspect of the present disclosure, a method for determining clone cell strain is provided that can include:
  obtaining a solid-phase carrier, cells and an antibody secreted by a clone cell strain;
  adsorbing the antibody secreted by the clone cell strain on the solid-phase carrier;
  incubating the cells and the antibody;
  preserving cells bound with the antibody;
  dyeing and counting the cells bound with the antibody; and
  determining the clone cell strain based on the cell count.

In still another aspect of the present disclosure, a kit for antibody or clone cell strain determination using above methods is provided that can include:
  a solid-phase carrier, which is used to adsorb an antibody which is to be tested or secreted by a clone cell strain to be tested;
  a coating buffer, in which the antibody is adsorbed on the solid-phase carrier;
  a cell washing solution, which is used to remove cells unbound with the antibody; and
  a dye solution, which is used to the dye cells bound with the antibody.

In yet another aspect of the present disclosure, a method for determining antibody specificity is provided that can include:
  obtaining a solid-phase carrier, cells and an antibody, the cells including at least two different known types cells;
  adsorbing the antibody on the solid-phase carrier;
  incubating the cells and the antibody;
  preserving cells bound with the antibody;
  dyeing and counting the cells bound with the antibody; and
  determining antibody specificity based on the cell count of the two different known type cells.

In the present disclosure, an antibody to be tested is bound with an antigen having natural conformation which is expressed on the surface of living cells, and then these cells are dyed and counted so as to determine antibody sensitivity or quality of clone cell strains in an antibody preparation. The method of the present disclosure may visually display binding level between an antibody and its natural antigen, so the determination may be more accurate and reduce labor and material costs caused by screening failures of positive clone cell strain. On the other hand, the method of the present disclosure may preliminarily determine antibody specificity based on distinguish the type of cells bound with the antibody to be tested.

DETAILED DESCRIPTION

An antibody is a kind of immunoglobulin having immune function and exists in body fluid and mediate humoral immunity, which is secreted by B cells when B cells proliferate and differentiate into plasma cells. An antibody can specifically bind with its antigen, such as pathogen, and display immune function after other immune molecules and cells participate. An antibody can be sorted as a monoclonal antibody and a polyclonal antibody. A monoclonal antibody has been widely used in biological and medical research field, because it has highly uniform physical and chemical property, unitary biological activity, excellent binding specificity, and could be easily produced. A monoclonal antibody can be used as a ligand in affinity chromatography, a guiding drug in biological treatment, immunosuppressive agents, a probe in research work, and the like, which already widely used in research, disease treatment and diagnosis. In clinical diagnosis, a monoclonal antibody is mainly used for detecting pathogens, tumor-specific antigen, tumor-associated antigens, and lymphocyte cell surface marker and trace components of human body.

In clinical diagnosis, quality of a monoclonal antibody directly determines the accuracy of detection result, and monoclonal antibody sensitivity against its antigen is an important indicator of the antibody quality. At present, a method for determining antibody sensitivity could be ELISA (Enzyme Linked Immunosorbent Assay), Western-blot, immunofluorescence test. But these methods have respective shortcoming.

In ELISA or Western-blot methods, antigens are produced from denatured proteins which are obtained after the cells are lysed, or from recombinant proteins, so that conformation of these antigens may be different from that of antigen having natural conformation. As result, the test results obtained by these methods just reflect binding sensitivity between the monoclonal antibody and denatured or recombinant antigens, but not that between the monoclonal antibody and the antigen having natural conformation. In particular, a false positive result may be obtained by these methods if epitope of the antigen for antibody binding is a conformational epitope, because space structure of the antigen may be destroyed by protein denaturation and the monoclonal antibody may not bind with the denatured protein.

An immunofluorescence test can include a direct immunofluorescence test and an indirect immunofluorescence test, and latter may need secondary antibodies. An immunofluorescence test can detect binding capacity between a monoclonal antibody and a protein having natural conformation. However, these tests may need long operation time and steps, and expensive test device, such as a fluorescence microscope or flow cytometry.

CN1660907A discloses three methods for determining a monoclonal antibody, which are indirect immunofluorescence test, speckle immunoblotting method and gold marker immune electron microscopy method. The indirect immunofluorescence test and gold marker immune electron microscopy method require costly devices for analyzing results. The speckle immunoblotting method needs a lysis solution of membrane proteins for adsorption so as to perform antigen-antibody reaction on a solid-phase such as nitrocellulose membrane. Therefore, determination result obtained by this method may not display antibody sensitivity between the monoclonal antibody and proteins having natural conformation, because the proteins in the lysis solution of membrane proteins may be denatured.

CN1718588A disclosed is a method where a monoclonal antibody is used to detect a malignant tumor. ELISA and immunoblotting techniques are used in the method. A recombinant protein is used as antigen for detection in ELISA techniques, and a denatured protein is used as antigen for detection in the immunoblotting techniques. Therefore, they cannot actually reflect antibody sensitivity between the monoclonal antibody and proteins having natural conformation.

CN101891806A discloses is a method for screening high quality monoclonal antibody by an indirect immunofluorescence test. The indirect immunofluorescence test needs expensive device such as a fluorescent microscope. This method could not be widely used in a small-size clinic or research institute because of such high cost.

In addition, there is a need for screening a positive done cell strain for obtaining a done cell strain which could secrete antibody having high sensitivity in antibody produce process. At present, widely used method is ELISA. However, the antibody secreted by the clone cell strain which is screened by ELISA may not be suitable for binding proteins having natural conformation, because a recombinant protein is uses as antigen in ELISA, and the screening failure may cause waste of labor and material resources.

CN1693461A discloses a method for screening a positive clone cell strain in monoclonal antibody preparation process by indirect ELISA. A recombinant protein is used as antigen in the method. The positive clone cell strain screened by this ELISA method may not actually really reflect antibody sensitivity between the monoclonal antibody and proteins having natural conformation, because the recombinant protein may not have natural conformation.

From above description, most of present methods for determining antibody sensitivity or screening positive clone cell strain use binding capacity between antibody and recombinant proteins or denatured proteins to reflect antibody sensitivity. But most of medical tests take advantage of a binding capacity between antibody and proteins having natural conformation. In order to accurately and quickly screen a monoclonal antibody which could have good binding capacity to proteins having natural conformation, there is a need to develop a new method for determining binding capacity between monoclonal antibodies and proteins having natural conformation.

The following example illustrates various features of the present invention but is not intended to in any way limit the scope of the invention as set forth in the claims.

DEFINITION

Unless otherwise specified, the following terms as used herein have the following meanings.

The term "antibody" as used herein has the broadest meaning and specifically covers intact monoclonal antibodies, polyclonal antibody, a multi-specific antibody (such as bis-specific antibody) formed by at least two intact antibodies, and antibody fragments etc., so long as they exhibit the desired biological activity.

The term "monoclonal antibody" as used herein refers to antibodies obtained by a substantially homogeneous population of antibody, that is, the each antibody of the population are identical except for minute quantity of naturally occurring antibody mutations. In addition, different from a polyclonal antibody which may binds different antigenic determinants (epitopes), each type of monoclonal antibody only binds a single antigenic determinant on an antigen. Besides their specificity, the superiority of the monoclonal antibody can be embodied in synthesis by the hybridoma culture so that there may be no other immunoglobulin pollution. The modifier "monoclonal" means the feature of antibody is obtained by a substantially homogeneous population of antibodies, and is not to be construed as requiring any particular method for the production of antibody.

A Method for Determining Antibody Sensitivity

In the present disclosure, a method for determining antibody sensitivity is provided that can include:
obtaining a solid-phase carrier, cells and an antibody;
adsorbing the antibody on the solid-phase carrier;
incubating the cells and the antibody;
preserving cells bound with the antibody;
dyeing and counting the cells bound with the antibody; and
determining the antibody sensitivity based on the cell count.

In step of obtaining a solid-phase carrier, cells and an antibody, the antibody to be tested may be monoclonal antibody or polyclonal antibody, monoclonal antibody is usually obtained; the solid-phase carrier may be wide-use polystyrene aperture plate or other common material such as cellulose, cross-linked dextran or the like. The form of solid-phase carrier may be test tubes or beans.

The cells may be living cells extracted from blood or tissue, such as mononuclear cells, lymphocytes or white cells from peripheral blood, or generation cells by cell culturing. Basically, in antibody sensitivity determination, it is already known what antigen or the small molecule against the antibody to be tested. In one embodiment of the present disclosure, cells who can express more antigen or small molecule on their cell surfaces are more suitable. For example, it is known that the lymphocytes express more CD3 or CD4 antigen on their cell surfaces, so lymphocytes are preferred when determining CD3 or CD4 antibody sensitivity. All sub-populations cells of leukocyte express CD45 antigen on their cell surfaces, so leukocytes could be used directly without further extraction of sub-populations.

A commercial cell extraction kit may be used to extract cells according the kit's operation instruction. Alternatively, cells may be extracted according to conventional method. For example, mononuclear cells may be extracted from peripheral blood by Percoll cell extraction solution; lymphocytes may be extracted from a peripheral blood by a lymphocyte extraction solution; leukocytes may be obtained from a peripheral blood after lysing red blood cells by hemolytic agent; cultural cells on walls of a culture flask may be firstly digested by an enzyme, and contracted by centrifugation; cultural cells in a culture medium may be directly contracted by centrifugation.

In general, the steps of a lymphocytes extraction method using a commercial lymphocyte extraction kit may include:
 mixing 1 ml of fresh anti-coagulation blood sample and 1 ml of Hanks' solution;
 carefully adding the mixture on the level surface of 2 ml of a lymphocyte extraction solution, centrifuging it for 15 minutes at 1500-2000 rpm/min. After centrifugation, there will be four cell layers in the centrifugal tube from top to bottom, each of the layer distribution is: the first is plasma or tissue homogenates layer, the second is cyclic opalescent lymphocyte layer, the third is transparent extraction solution layer, the fourth is a red blood cell layer.
 collecting the second layer cells and placing them into a test tube containing cell washing solution, mixing thoroughly, and then centrifuging it for 10-15 minutes at 1500-2000 rpm/min. the desired cells will be obtained after washing the precipitation for 2 times.

In the step of adsorbing the antibody on the solid-phase carrier, the antibody and the coating buffer is mixed to obtain an antibody solution, and the antibody solution and the solid-phase carrier contact each other. For example, the antibody solution are added into a plate well of a polystyrene porous plate, such as a 96-well polystyrene plate, and placed at an incubator with 37° C. for 1-2 h or incubated at 4° C. for overnight. The adsorption between the antibody and the carrier is physical; the force of adsorption is the acting force between hydrophobic groups of a protein molecular and those on the surface of the solid-phase carrier. This kind of acting force is not specific, which depends on the pH value, temperature, protein concentration, ionic concentration, and adsorption time. In addition, the solid-phase carrier has different adsorption capacity to different proteins. Macro-molecular proteins may be easier to adsorb the surface of solid-phase carrier than micro-molecular proteins, because the former might have more hydrophobic groups than the latter. The coating buffer may be carbonate buffer, citrate buffer or Tris-HCl buffer or the like. In one embodiment, the carbonate buffer is used as coating buffer, whose pH value may range 8-10, such as 9-10, or alternatively 9.5-10. In one embodiment, the ionic concentration of coating buffer may range 0.01-1 mol/L, such as 0.01-0.5 mol/L, or alternatively 0.05-0.1 mol/L. The amount of antigen coated on the 96-well polystyrene plate may range 2-50 μg/μlate, such as 5-20 μg/μlate, or alternatively 5-10 μg/μlate.

In steps of incubating the cells and the antibody adsorbed on the solid-phase carrier and preserving cells bound with the antibody adsorbed on the solid-phase carrier, the cells are firstly prepared as cell suspension, whose cell concentration could range 5-500 cells/μl, such as 10-100 cells/μl, or alternatively 50-80 cells/μl. The cell suspension and the solid-phase carrier adsorbed antibody contact each other. Target cells are caught by the antibody adsorbed on the carrier through binding force between the antibody and the antigen or small molecule on the cell surface. After incubation for a period of time and washing by Hanks' solution, cells which have no antigen against the antibody could be washed away, at the same time, cells which have antigen against the antibody could be preserved. In one embodiment, a 96-well polystyrene plate is used as carrier during contact of antibody and living cell, the volume of the cell suspension added into each well could be 100 μl. The incubation may be performed with gentle shaking at room temperature for about 1 hour, such as 20-40 minutes, or alternatively 20-30 minutes.

After binding reaction of antibody and cells, unbound cells are washed away using a cell washing solution. Many washing solutions could be suitable, such as PBS buffer, PBS buffer containing BSA, or PBS buffer containing calf serum or the like. In one embodiment, PBS buffer containing BSA is used, where the concentration of BSA could range 0.1-1 g/L. If the 96-well polystyrene plate is used as a carrier, the volume of the cell washing solution for each washing could range 100-300 μl, such as 200 μl. In washing step, 200 μl of the washing solution is added into each well for each washing, gently aspirated and blown out for several times, followed by removed from the well. The washing step may be repeated three times. After cell washing, the reminder in the well is removed for next dyeing.

Figure 1:
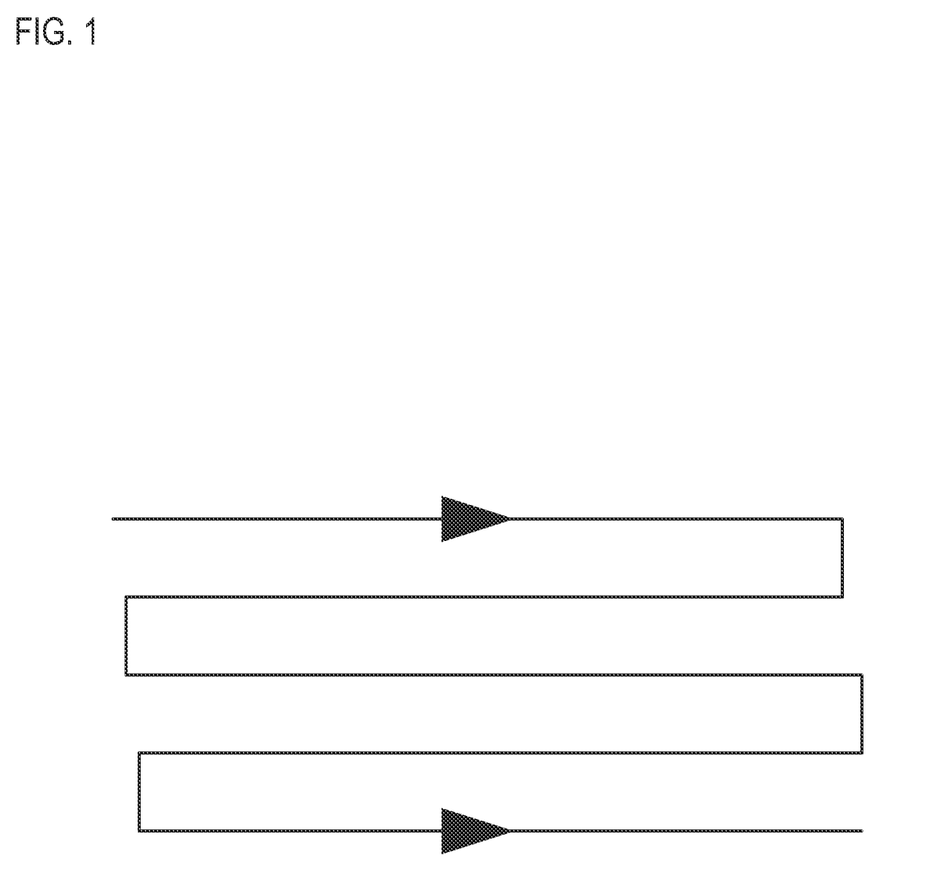
FIG. 1 is a schematic diagram of "rampart type" cell counting method, a method used for counting cells used in accordance with an embodiment of the present disclosure.

In the step of dyeing and counting the cells bound with the antibody, a cell dye, such as nucleic acid dye, is used to dye the living cells which bind the solid-phase carrier. The nucleic acid dye could bind the nucleic acid in the cells so as to make cells to have visually identified color. The nucleic acid dye may include methyl chloride, Switzerland Giemsa solution, sand yellow, hematoxylin. In one embodiment, methyl chloride, Switzerland Giemsa solution or hematoxylin is used as cell dye. The methyl chloride is dissolved in water to prepare dye solution whose methyl chloride contraction range 0.05-5%, such as 0.05-1.5%, or alternatively, 0.05-0.5%. Switzerland Giemsa solution and hematoxylin dye solution are commercially available. In one embodiment, before cell dyeing, the cells bound on the 96-well polystyrene plate in each well are fixed by 50 μl of 4% of formaldehyde (pH 7.0). The fixing solution does not need to be removed, 50-100 μl of dye solution is added into each well followed by placing at room temperature for 5-15 minutes. In order to accelerate dyeing, the bottom of the 96-well polystyrene plate may be heated for 1-2 minutes by a hairdryer. And then, the dyeing solution is aspirated from the well by a plastic suction pipe followed by adding pure water by a plastic suction pipe. This aspiration-adding step is repeated two times for washing away the dye solution. The 96-well polystyrene plate is put upside down for drying the reminder liquid in the well. The cells on each well are counted by an ordinary invert microscope using "rampart type" cell counting method. The antibody sensitivity is determined based on the cell count under the microscope, the higher the cell count, the higher the antibody sensitivity. The accuracy of determination may be improved by performing a positive control and a negative control.

A Method for Determining Clone Cell Strain

In the present disclosure, a method for determining clone cell strain is provided that can include:

obtaining a solid-phase carrier, cells and an antibody secreted by a clone cell strain;

adsorbing the antibody secreted by the clone cell strain on the solid-phase carrier;

incubating the cells and the antibody adsorbed on the solid-phase carrier;

preserving cells bound with the antibody;

dyeing and counting the cells bound with the antibody; and determining the clone cell strain based on the cell count.

The culture supernatant of the clone cell strain to be tested is obtained, which contain the secreted antibody. The cell count could be obtained by above method for determining antibody sensitivity. The higher the cell count, the better the sensitivity between the antibody secreted by the clone cell strain and the antigen having natural conformation (i.e. the better quality of the clone cell strain). It is helpful to improve screening successes rate of clone cell strain by picking strains having higher cell count for cultivation.

A Kit for Antibody or Clone Cell Strain Determination

In the present disclosure, a kit for antibody or clone cell strain determination using above method is provided that can include:

a solid-phase carrier, which is used to adsorb an antibody which is to be tested or secreted by a clone cell strain to be tested;

a coating buffer, in which the antibody is adsorbed on the solid-phase carrier;

a cell washing solution, which is used to remove cells unbound with the antibody; and a dye solution, which is used to dye the cells bound with the antibody.

The detail descriptions of a solid-phase carrier, a coating buffer, a cell washing solution, and dyeing solution are similar to those of above embodiment.

A Method for Determining Antibody Specificity

In the present disclosure, a method for determining antibody specificity is provided that can include:

obtaining a solid-phase carrier, cells and an antibody, the cells including at least two different known types cells;

adsorbing the antibody on the solid-phase carrier;

incubating the cells and the antibody adsorbed on the solid-phase carrier;

preserving cells bound with the antibody adsorbed on the solid-phase carrier;

dyeing and counting the cells bound with the antibody; and determining the antibody sensitivity based on the cell count of the two different known type cells.

The detail descriptions of steps and reagents are the similar to those of above embodiment. In one embodiment, lymphocytes and mononuclear cells are chosen to determine CD14 antibody specificity. A dye solution which can distinguish lymphocytes and mononuclear cells could be used as the dye solution, or alternatively, a dye solution which is specific to one of lymphocytes and mononuclear cells could be used as the dye solution. The difference between cell counts of these two kinds of cells could be used to determine binding specificity of the CD14 antibody against mononuclear cells. It is known that mononuclear cells express much more CD14 antigen than lymphocytes does. If lymphocyte counting number is much more than a normal number, the binding specificity of this antibody to be tested to CD14 antigen will be determined to be unsatisfactory. For example, if lymphocyte counting number is 20 cells when the determination is performed using a satisfactory CD14 antibody, an antibody to be tested will be determined to be unsatisfactory when the lymphocyte counting number of the antibody is 50.

EXAMPLES

The following example illustrates various features of the present invention but is not intended to in any way limit the scope of the invention as set forth in the claims.

Unless otherwise specified, in the following examples, the components of reagent used are analytically pure, the dissolvent is deionized water, the device for cell counting is NIKON ANTI-MOULD invert microscope with 100×10 magnification, the counting method is shown in the FIG. 1. The volume of each well of 96-well polystyrene plate is 400 µl.

Example 1

Figure 2:
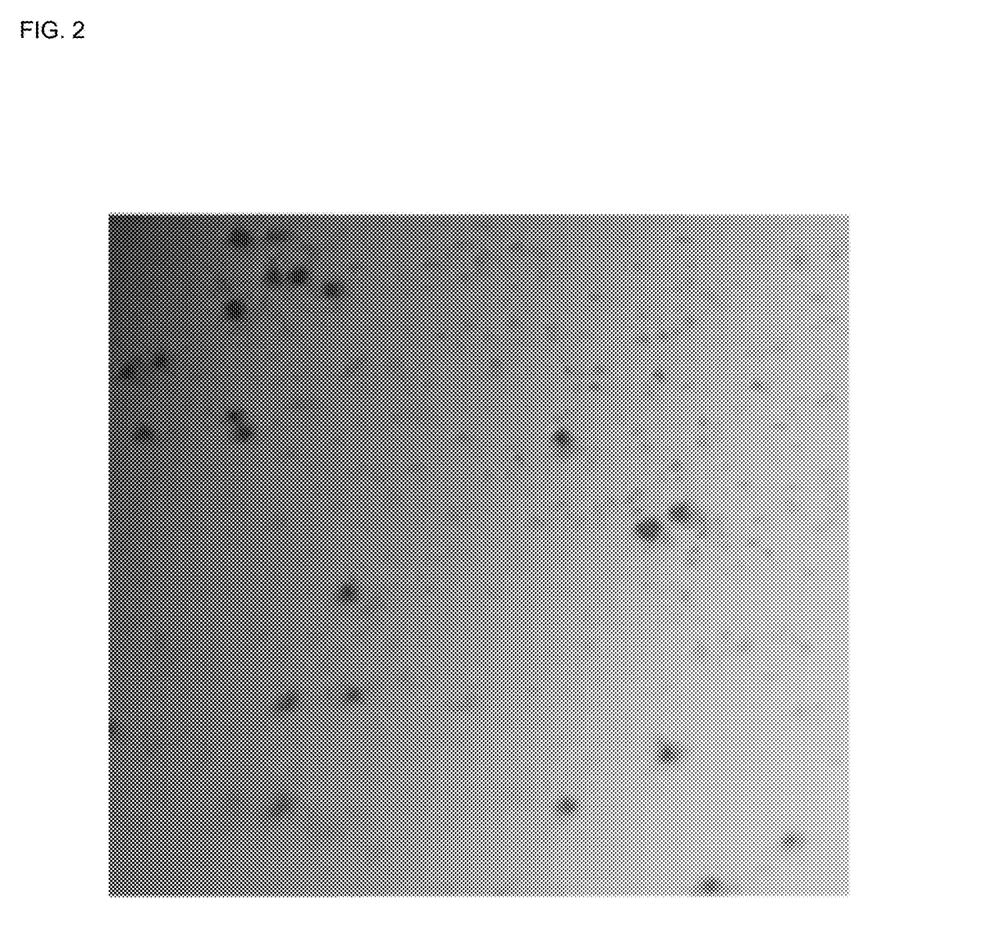
FIG. 2 is a picture depicting dyed cells bound to an antibody, in accordance with Example 1 of the present disclosure.

A mouse anti-human CD3 monoclonal antibody to be tested, a mouse anti-human CD3 monoclonal antibody which was determined to be satisfactory (positive control), and mouse IgG which basically does not bind with CD3 antigen (negative control) were coated on a 96-well polystyrene plate in 10 µg/µlate. Each sample was tested in double wells. The coating buffer was carbonate buffer with pH 9.8. The plate was placed in a incubator with 37° C. for 1 hour. After coating, the plate was placed upside down on the clean towel and dried. 100 µl of lymphocyte suspension whose concentration was $6 \times 10^7$ cells/L was added into each well of the plate, and the plate was gently shaken for 30 minutes in a shaking table. After binding reaction, a cell washing solution was added into each well. 200 µl of the cell washing solution was added into each well each time for each washing, gently aspirated and blown out for several times, followed by removed from the well. The washing step is repeated three times. The cells bound on the 96-well polystyrene plate were fixed by 50 µl of 4% of formaldehyde (pH 7.0), and dyed by directly adding 50 µl of 0.25% methyl chloride. After dyeing 5 minutes at room temperature, the dyeing solution was aspirated from the well by a plastic suction pipe followed by adding pure water by the plastic suction pipe. This aspiration-adding step was repeated two times for washing away the dye solution. The 96-well polystyrene plate was put upside down for drying the reminder liquid in the well. The cells on each well were counted by a microscope. The dyed cell picture under the microscope was shown in FIG. 2; the cell count are: 248 and 257 dyed cells were counted in wells of antibody to be tested, 240 and 245 dyed cells were counted in wells of the positive control, and 23 and 27 dyed cells were counted in wells of negative control. This example shows that lymphocyte expresses CD3 antigen and the sensitivity of antibody to be test against CD3 antigen could be determined by counting lymphocytes.

Example 2

Two clone cell strains to be tested which secreted mouse anti-human CD4 antibody and mouse IgG (negative control) were coated on a 96-well polystyrene plate in 5 µg/µlate.

Figure 3:
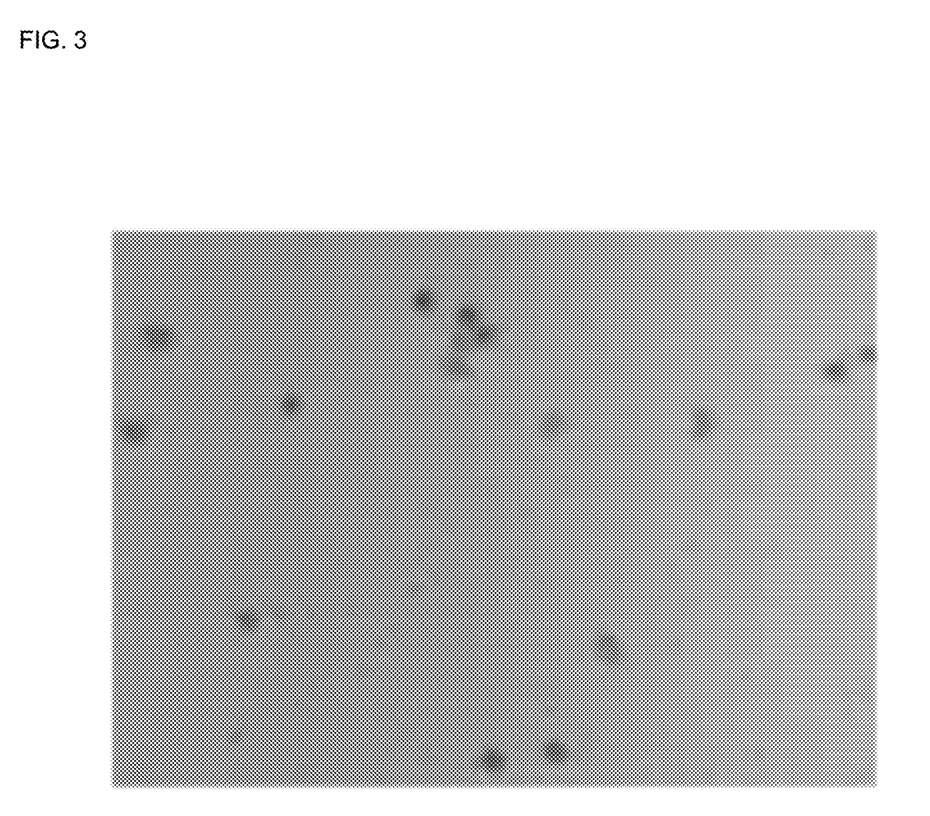
FIG. 3 is a picture depicting dyed cells bound to an antibody, in accordance with Example 2 of the present disclosure.

Each sample was tested in double wells. The coating buffer was carbonate buffer with pH 9.0. The plate was placed in a incubator with 37° C. for 1.5 hour. After coating, the plate was placed upside down on the clean towel and dried. 100 µl of lymphocyte suspension whose concentration was $6 \times 10^8$ cells/L was added into each well of the plate, and the plate was gently shaken for one hour in a shaking table. A cell washing solution was added to wash away unbound cells. 200 µl of the cell washing solution was added into each well each time for each washing, gently aspirated and blown out by a transferpettor having 200 µl measurement range, followed by removed from the well. The washing step is repeated three times. The cells bound on the 96-well polystyrene plate were fixed by 50 µl of 4% of formaldehyde (pH 7.0), and dyed by directly adding 100 µl of 0.05% methyl chloride. After dyeing 3 minutes at room temperature, the dyeing solution was aspirated from the well by a plastic suction pipe followed by adding pure water by the plastic suction pipe. This aspiration-adding step was repeated two times. The 96-well polystyrene plate was put upside down for drying the reminder liquid in the well. The cells on each well were counted by a microscope. The dyed cell picture under the microscope was shown in FIG. 3; the cell count are: 110 and 117 dyed cells were counted which bound the CD4 antibody secreted by the first strain to be tested, 24 and 27 dyed cells were counted in the well of the second strain to be tested, and 10 and 17 dyed cells were counted in wells of negative control. Comparing cell count of two stains, it is shown that the first clone cell strain has better secretion capacity of CD4 antibody and/or its antibody has better antibody sensitivity to be worth of further cultivation.

Example 3

Figure 4:
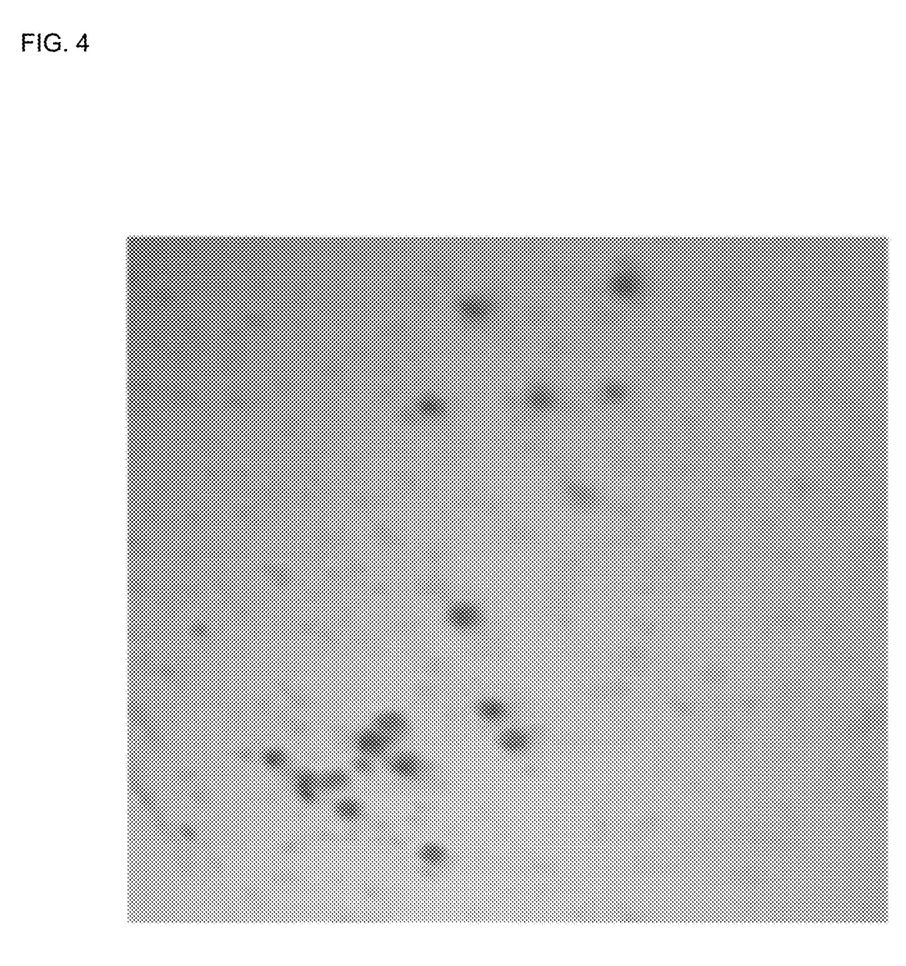
FIG. 4 is a picture depicting dyed cells bound to an antibody, in accordance with Example 3 of the present disclosure.

A mouse anti-human CD45 monoclonal antibody to be tested, a mouse anti-human CD45 monoclonal antibody which was determined to be satisfactory (manufactured by Ebioscience Company), and mouse IgG were coated on a 96-well polystyrene plate in 20 µg/µlate. Each sample was tested in double wells. The coating buffer was Tris-HCl buffer with pH 9.0. The plate was placed at 4° C. for overnight. After coating, the plate was placed upside down on the clean towel and dried. 100 µl of leukocyte suspension whose concentration was $7.2 \times 10^8$ cells/L was added into each well of the plate, and the plate was gently shaken for one hour in a shaking table. A cell washing solution was added to wash away leukocytes unbound with the monoclonal antibody. 200 µl of the cell washing solution was added into each well each time for each washing, gently aspirated and blown out by a transferpettor having 200 µl measurement range, followed by removed from the well. The washing step is repeated three times. The cells bound on the 96-well polystyrene plate were fixed by 50 µl of 4% of formaldehyde (pH 7.0), and dyed by directly adding 100 µl of 0.2% methyl chloride. After dyeing 3 minutes at room temperature, the dyeing solution was aspirated from the well by a plastic suction pipe followed by adding pure water by the plastic suction pipe. This aspiration-adding step was repeated two times. The 96-well polystyrene plate was put upside down for drying the reminder liquid in the well. The cells on each well were counted by a microscope. The dyed cell picture under the microscope was shown in FIG. 4; the cell count are: 653 and 662 dyed cells were counted in wells of antibody to be tested, 630 and 625 dyed cells were counted in wells of CD45 antibody manufactured by Ebioscience Company, and 12 and 15 dyed cells were counted in wells of negative control. This example shows that sub-populations cells of leukocyte express CD45 antigen and the sensitivity of antibody to be test against CD45 antigen could be determined by counting leukocytes.

Example 4

Figure 5:
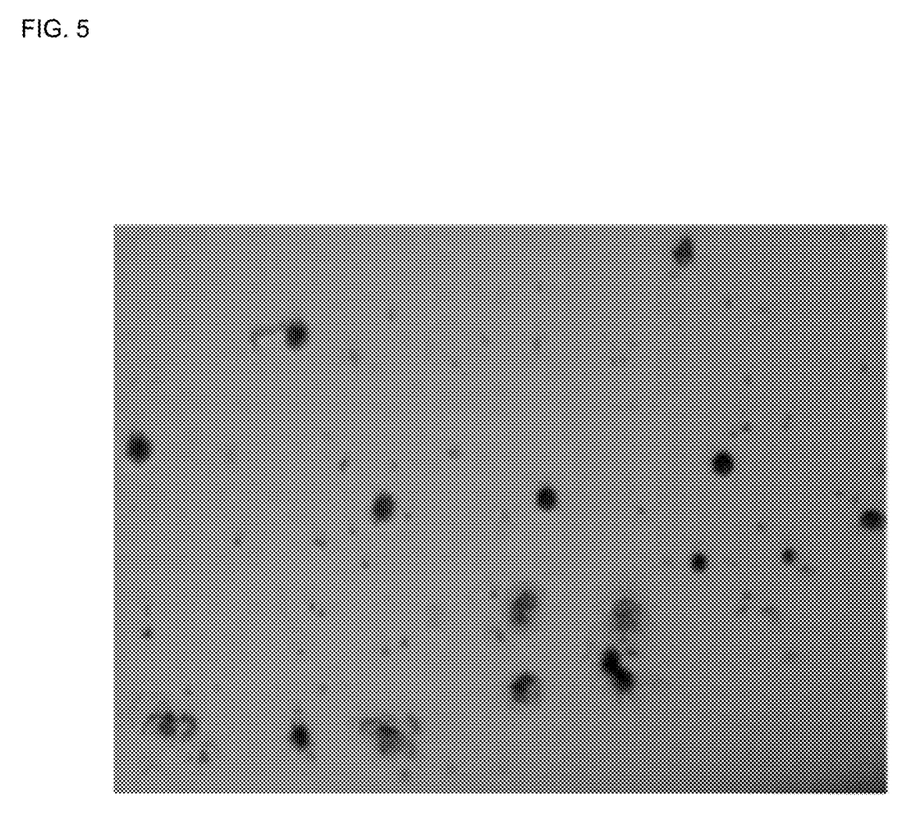
FIG. 5 is a picture depicting dyed cells bound to an antibody, in accordance with Example 4 of the present disclosure.

A mouse anti-human CD45 monoclonal antibody to be tested, a mouse anti-human CD45 monoclonal antibody which was determined to be satisfactory (manufactured by Ebioscience Company), and mouse IgG were coated on a 96-well polystyrene plate in 10 µg/µlate. Each sample was tested in double wells. The coating buffer was carbonate buffer with pH 9.6. The plate was placed at 4° C. for overnight. After coating, the plate was placed upside down on the clean towel and dried. 100 µl of leukocyte suspension whose concentration was $5 \times 10^7$ cells/L was added into each well of the plate, and the plate was gently shaken for 20 minutes in a shaking table. A cell washing solution was added to wash away leukocytes unbound with the monoclonal antibody. 200 µl of the cell washing solution was added into each well each time for each washing, gently aspirated and blown out by a transferpettor having 200 µl measurement range, followed by removed from the well. The washing step is repeated three times. The cells bound on the 96-well polystyrene plate were fixed by 50 µl of 4% of formaldehyde (pH 7.0), and dyed by directly adding 100 µl of Switzerland Giemsa solution. After dyeing 15 minutes at room temperature, the dyeing solution was aspirated from the well by a plastic suction pipe followed by adding pure water by the plastic suction pipe. This aspiration-adding step was repeated two times. The 96-well polystyrene plate was put upside down for drying the reminder liquid in the well. The cells on each well were counted by a microscope. The dyed cell picture under the microscope was shown in FIG. 5; the cell count are: 420 and 430 dyed cells were counted in wells of antibody to be tested, 410 and 425 dyed cells were counted in wells of CD45 antibody manufactured by Ebioscience Company, and 10 and 14 dyed cells were counted in wells of negative control. This example shows that different dye solutions also can be used in the methods of the present disclosure, as long as the dye solution can properly dye the target cells.

Example 5

Figure 6:
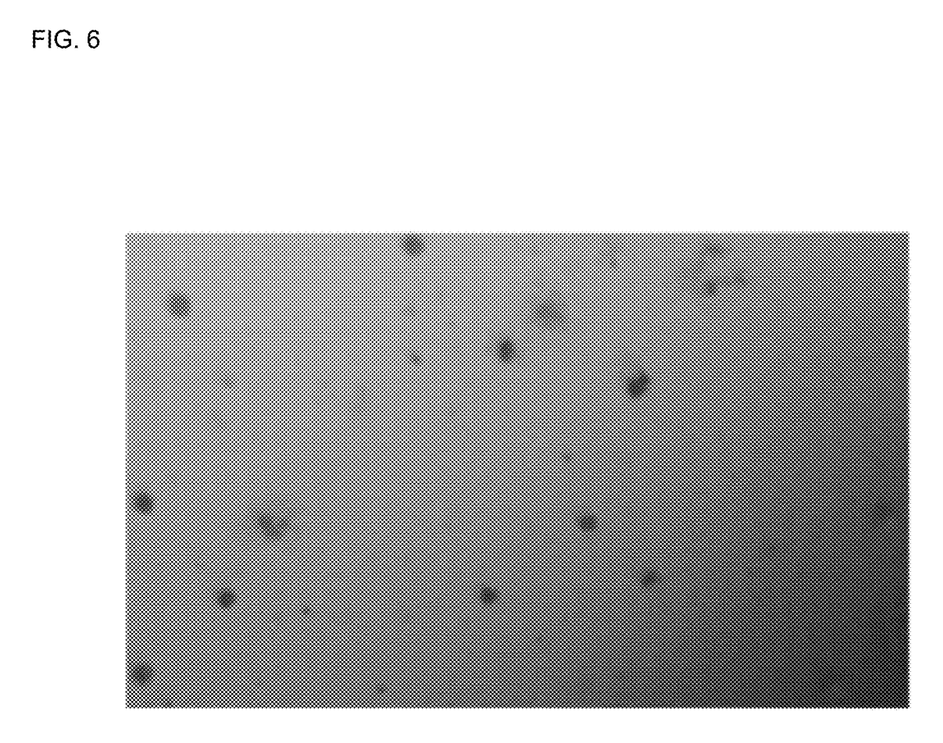
FIG. 6 is a picture depicting dyed cells bound to an antibody, in accordance with Example 5 of the present disclosure.

A mouse anti-human CD45 monoclonal antibody to be tested, a mouse anti-human CD45 monoclonal antibody which was determined to be satisfactory (manufactured by Ebioscience Company), and mouse IgG were coated on a 96-well polystyrene plate in 10 µg/µlate. Each sample was tested in double wells. The coating buffer was carbonate buffer with pH 9.6. The plate was placed at 4° C. for overnight. After coating, the plate was placed upside down on the clean towel and dried. 100 µl of leukocyte suspension whose concentration was $6 \times 10^7$ cells/L was added into each well of the plate, and the plate was gently shaken for 20 minutes in a shaking table. A cell washing solution was added to wash away leukocytes unbound with the monoclonal antibody. 200 µl of the cell washing solution was added into each well each time for each washing, gently aspirated and blown out by a transferpettor having 200 µl measurement range, followed by removed from the well. The washing step is repeated three times. The cells bound on the 96-well polystyrene plate were fixed by 50 µl of 4% of formaldehyde (pH 7.0), and dyed by directly adding 100 µl of hematoxylin solution. After dyeing 15 minutes at room temperature, the dyeing solution was aspirated from the well by a plastic suction pipe followed by adding pure water by the plastic suction pipe. This aspiration-adding step was repeated two times. The 96-well polystyrene plate was put upside down for drying the reminder liquid in the well. The cells on each well were counted by a microscope. The dyed cell picture under the microscope was shown in FIG. 6; the cell count are: 550 and 561 dyed cells were counted in wells of antibody to be tested, 541 and 555 dyed cells were counted in wells of CD45 antibody manufactured by Ebioscience Company, and 15 and 17 dyed cells were counted in wells of negative control. This example shows that different dye solutions also can be used in the methods of the present disclosure, as long as the dye solution can properly dye the target cells.

Example 6

Figure 7:
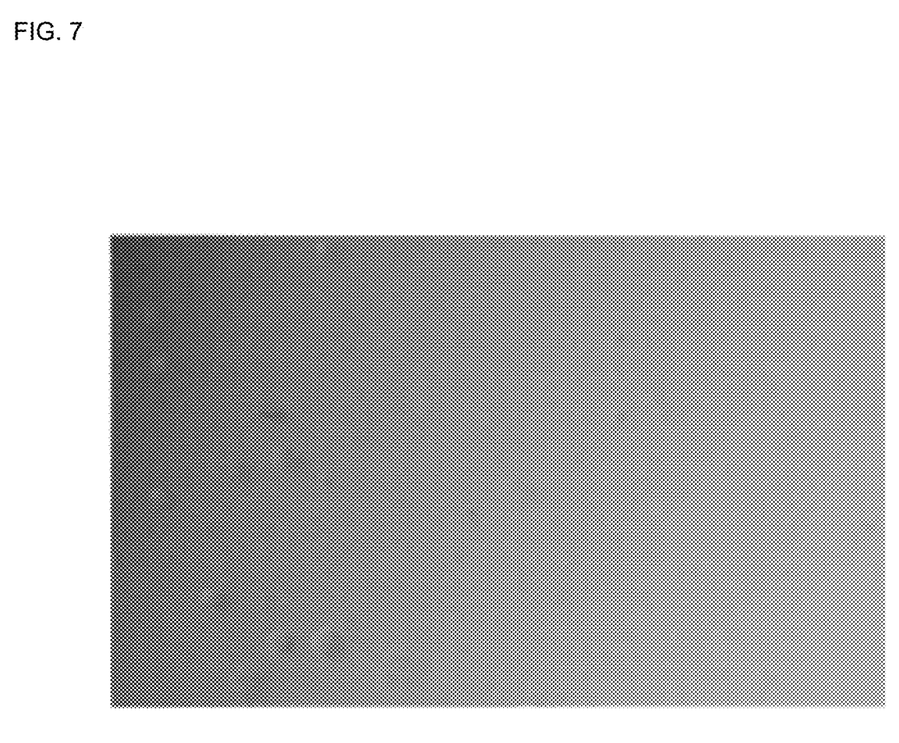
FIG. 7 is a picture depicting dyed cells bound to an antibody, in accordance with Example 6 of the present disclosure.

A mouse anti-human CD45 monoclonal antibody to be tested, a mouse anti-human CD45 monoclonal antibody which was determined to be satisfactory (manufactured by Ebioscience Company), and mouse IgG were coated on a 96-well polystyrene plate in 10 μg/μlate. Each sample was tested in double wells. The coating buffer was carbonate buffer with pH 9.6. The plate was placed at 4° C. for overnight. After coating, the plate was placed upside down on the clean towel and dried. 100 μl of leukocyte suspension whose concentration was $6 \times 10^7$ cells/L was added into each well of the plate, and the plate was gently shaken for 20 minutes in a shaking table. A cell washing solution was added to wash away leukocytes unbound with the monoclonal antibody. 200 μl of the cell washing solution was added into each well each time for each washing, gently aspirated and blown out by a transferpettor having 200 μl measurement range, followed by removed from the well. The washing step is repeated three times. The cells bound on the 96-well polystyrene plate were fixed by 50 μl of 4% of formaldehyde (pH 7.0), and dyed by directly adding 100 μl of sand yellow solution. After dyeing 15 minutes at room temperature, the dyeing solution was aspirated from the well by a plastic suction pipe followed by adding pure water by the plastic suction pipe. This aspiration-adding step was repeated two times. The 96-well polystyrene plate was put upside down for drying the reminder liquid in the well. The cells on each well were counted by a microscope. The dyed cell picture under the microscope was shown in FIG. 7; the cell count are: 525 and 531 dyed cells were counted in wells of antibody to be tested, 536 and 531 dyed cells were counted in wells of CD45 antibody manufactured by Ebioscience Company, and 14 and 17 dyed cells were counted in wells of negative control. This example shows that different dye solutions also can be used in the methods of the present disclosure, as long as the dye solution can properly dye the target cells.

Example 7

Figure 8:
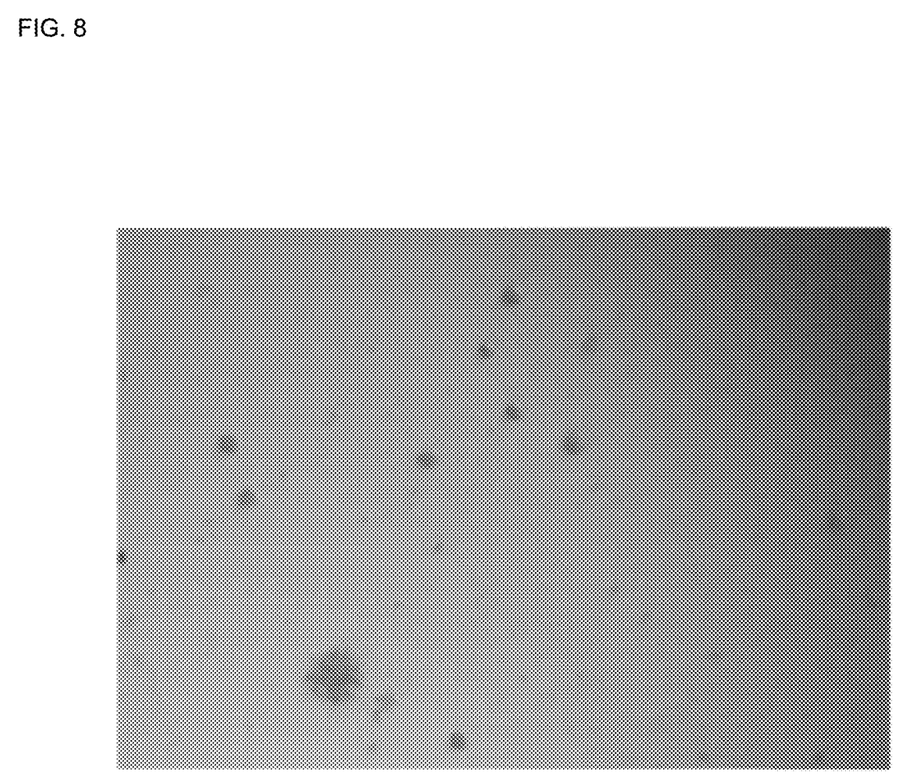
FIG. 8 is a picture depicting dyed cells bound to an antibody, in accordance with Example 7 of the present disclosure.

A mouse anti-human CD19 monoclonal antibody to be tested, a mouse anti-human CD19 monoclonal antibody which was determined to be satisfactory (positive control), and mouse IgG were coated on a 96-well polystyrene plate in 20 μg/μlate. Each sample was tested in double wells. The coating buffer was carbonate buffer with pH 10.0. The plate was placed at 37° C. for 2 hours. After coating, the plate was placed upside down on the clean towel and dried. 100 μl of lymphocyte suspension whose concentration was $6 \times 10^7$ cells/L was added into each well of the plate, and the plate was gently shaken for 20 minutes in a shaking table. A cell washing solution was added to wash away leukocytes unbound with the monoclonal antibody. 200 μl of the cell washing solution was added into each well each time for each washing, gently aspirated and blown out by a transferpettor having 200 μl measurement range, followed by removed from the well. The washing step is repeated three times. The cells bound on the 96-well polystyrene plate were fixed by 50 μl of 4% of formaldehyde (pH 7.0), and dyed by directly adding 100 μl of 0.2% methyl chloride. After dyeing 5 minutes at room temperature, the dyeing solution was aspirated from the well by a plastic suction pipe followed by adding pure water by the plastic suction pipe. This aspiration-adding step was repeated two times. The 96-well polystyrene plate was put upside down for drying the reminder liquid in the well. The cells on each well were counted by a microscope. The dyed cell picture under the microscope was shown in FIG. 8; the cell count are: 25 and 21 dyed cells were counted in wells of antibody to be tested, 125 and 130 dyed cells were counted in wells of positive control, and 16 and 14 dyed cells were counted in wells of negative control. This example shows that the methods of present disclosure not only can determine antibody having higher sensitivity but also can determine antibody having poor sensitivity, and have good universal property.

Example 8

Figure 9:
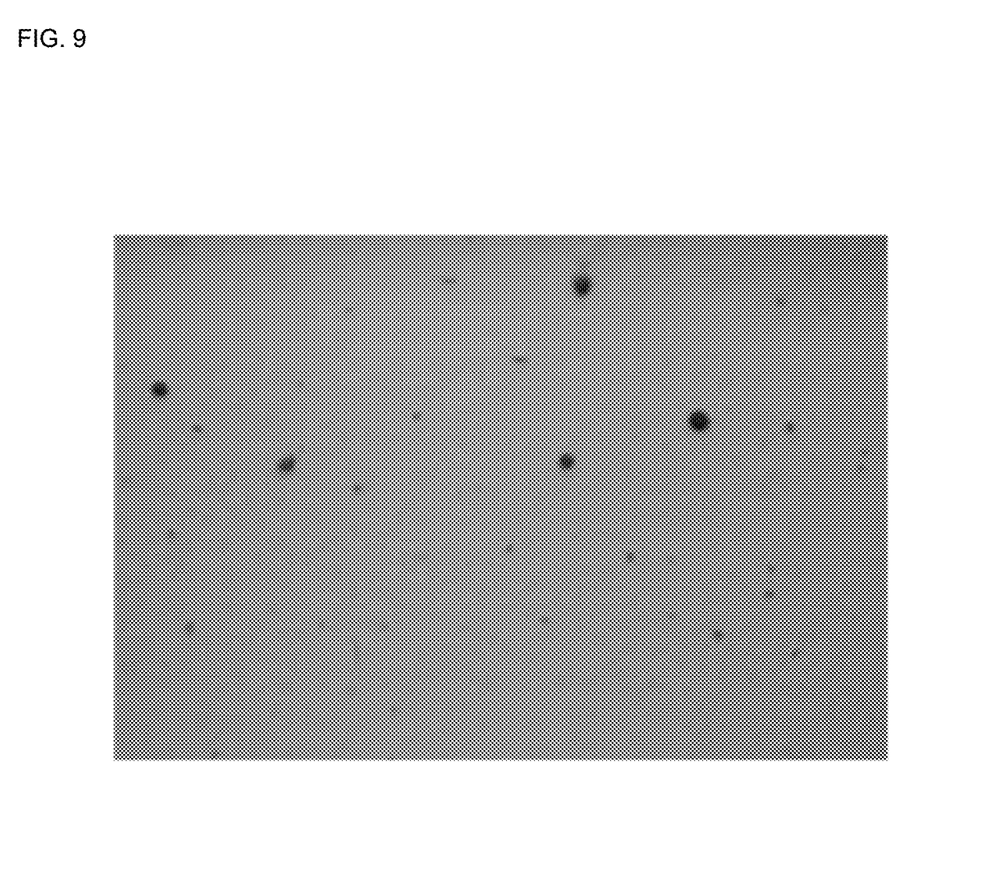
FIG. 9 is a picture depicting dyed cells bound to an antibody, in accordance with Example 8 of the present disclosure.

A mouse anti-human CD3 monoclonal antibody to be tested, a mouse anti-human CD3 monoclonal antibody which was determined to be satisfactory (positive control), and mouse IgG were coated on a 96-well polystyrene plate in 10 μg/μlate. Each sample was tested in double wells. The coating buffer was carbonate buffer with pH 9.0. The plate was placed at 37° C. for 1.5 hours. After coating, the plate was placed upside down on the clean towel and dried. 100 μl of lymphocyte suspension whose concentration was $5 \times 10^7$ cells/L was added into each well of the plate, and the plate was gently shaken for 30 minutes in a shaking table. A cell washing solution was added to wash away leukocytes unbound with the monoclonal antibody. 200 μl of the cell washing solution was added into each well each time for each washing, gently aspirated and blown out by a transferpettor having 200 μl measurement range, followed by removed from the well. The washing step is repeated three times. The cells bound on the 96-well polystyrene plate were fixed by 50 μl of 4% of formaldehyde (pH 7.0), and dyed by directly adding 100 μl of hematoxylin solution. After dyeing 15 minutes at room temperature, the dyeing solution was aspirated from the well by a plastic suction pipe followed by adding pure water by the plastic suction pipe. This aspiration-adding step was repeated two times. The 96-well polystyrene plate was put upside down for drying the reminder liquid in the well. The cells on each well were counted by a microscope. The dyed cell picture under the microscope was shown in FIG. 9; the cell count are: 51 and 42 dyed cells were counted in wells of CD3 antibody to be tested, 251 and 254 dyed cells were counted in wells of positive control, and 19 and 13 dyed cells were counted in wells of negative control. This example shows that the methods of present disclosure not only can determine antibody having higher sensitivity but also can determine antibody having poor sensitivity, and have good universal property.

In the present disclosure, an antibody to be tested is bound with an antigen having natural conformation which is expressed on the surface of living cells, and then these cells are dyed and counted so as to determine antibody sensitivity or quality of clone cell strains in an antibody preparation.

The method of the present disclosure may visually display bounding level between an antibody and its natural antigen, so the determination may be more accurate and reduce labor and material costs caused by screening failures of positive clone cell strain. On the other hand, the method of the present disclosure may preliminarily determine antibody specificity based on distinguish the type of cells bound with the antibody to be tested. These embodiments and examples show that methods of the present disclosure have good universal property.

The data, figures, instruments, reagents and steps herein should be understood to be illustrative, but not restrictive. Although the present disclosure was described with references to the above concrete embodiments, many modifications and variances will be apparent to skilled persons in the art. All the modifications and variances also fall within the spirit and scope of the disclosure.

The invention claimed is:

1. A method for determining antibody binding sensitivity, comprising:
    obtaining a solid-phase carrier, cells and an antibody;
    adsorbing the antibody on the solid-phase carrier to form an adsorbed antibody;
    incubating the cells and the adsorbed antibody;
    washing the solid-phase to preserve cells bound with the adsorbed antibody;
    dyeing the cells bound with the adsorbed antibody with a dye to obtain stained cells;
    counting the stained cells one by one to obtain a number of the stained cells; and
    determining the antibody binding sensitivity based on the number of the stained cells in comparison to a positive control and a negative control, wherein the higher the number of the stained cells as compared to the negative control, the better the antibody binding sensitivity.

2. The method according to claim 1, wherein counting the stained cells one by one is performed under a microscope.

3. The method according to claim 1, wherein said cells are cells from body fluid of human or animal; or primary or generation cells that are obtained by cell culturing.

4. The method according to claim 3, wherein said cells from body fluid of human or animal are selected from the group consisting of red blood cells, leukocytes and platelets.

5. The method according to claim 4, wherein said cells are lymphocytes.

6. The method according to claim 1, wherein the antibody is a monoclonal antibody.

7. The method according to claim 1, wherein said solid-phase carrier is selected from the group consisting of cellulose, cross-linked dextran and polystyrene.

8. The method according to claim 1, wherein the cells are prepared as a cell suspension having a concentration ranging from 5-500 cells/µl.

9. The method according to claim 1, wherein the cells and the adsorbed antibody are incubated at 20° C.-25° C. for one hour.

10. The method according to claim 1, wherein:
    before adsorbing the antibody on the solid-phase carrier, the antibody is mixed with a coating buffer having a pH value ranging from 6-8.

11. The method according to claim 10, wherein said coating buffer has an ionic concentration ranging from 0.01-1 mol/L.

12. The method according to claim 1,
    wherein the dye is selected from the group consisting of methyl chloride, Switzerland Giemsa solution, sand yellow and hematoxylin.

13. The method according to claim 12, wherein the methyl chloride is dissolved in water with a concentration ranging from 0.05-5%.

14. The method according to claim 1, further comprising:
    fixing the cells bound with the antibody before dyeing the cells.

15. The method according to claim 1, further comprising:
    performing a positive and/or negative control, which comprises:
        providing an antibody with known binding sensitivity as a positive and/or negative antibody;
        adsorbing the positive and/or negative antibody on the solid-phase carrier;
        incubating the cells and the positive and/or negative antibody;
        washing the solid-phase to preserve cells bound with the positive and/or negative antibody;
        dyeing and counting the cells bound with the positive and/or negative antibody.

16. The method according to claim 1, wherein said antibody is a monoclonal antibody against antigen expressed on a cell surface.

17. The method according to claim 1, wherein said antibody is a monoclonal antibody against surface antigen of lymphocyte.

* * * * *